(12) United States Patent
Huang et al.

(10) Patent No.: US 7,488,859 B2
(45) Date of Patent: Feb. 10, 2009

(54) METHOD FOR PRODUCING ADAMANTANE

(75) Inventors: Ming-Yu Huang, Chiayi (TW); Jann-Chen Lin, Chiayi (TW); Kun-Hai Lin, Chiayi (TW); Jung-Chung Wu, Chiayi (TW)

(73) Assignee: CPC Corporation, Taiwan, Taipei (TW)

( * ) Notice: Subject to any disclaimer, the term of this patent is extended or adjusted under 35 U.S.C. 154(b) by 43 days.

(21) Appl. No.: 11/812,543

(22) Filed: Jun. 20, 2007

(65) Prior Publication Data

US 2008/0319241 A1   Dec. 25, 2008

(51) Int. Cl.
*C07C 5/13* (2006.01)
*C07C 13/28* (2006.01)

(52) U.S. Cl. .................. 585/352; 585/734; 585/741; 585/747; 585/748; 585/749

(58) Field of Classification Search .............. 585/734, 585/741, 742, 747, 748, 749
See application file for complete search history.

(56) References Cited

U.S. PATENT DOCUMENTS

| | | | |
|---|---|---|---|
| 3,894,099 A | * | 7/1975 | Takaishi et al. ............. 585/352 |
| 3,944,626 A | * | 3/1976 | Honna et al. ................ 585/352 |
| 4,086,284 A | * | 4/1978 | Schneider et al. ........... 585/360 |

* cited by examiner

*Primary Examiner*—Glenn Caldarola
*Assistant Examiner*—In Suk Bullock
(74) *Attorney, Agent, or Firm*—Finnegan, Henderson, Farabow, Garrett & Dunner, L.L.P.

(57) ABSTRACT

A method for producing adamantane includes isomerizing exo-tetrahydrodicyclopentadiene into adamantane in an acidic chloroaluminate ionic liquid composed of aluminum (III) trichloride and a quaternary ammonium halide having a quaternary ammonium cation selected from a group consisting of tetraalkylammonium, dialkylpyridinium, and trialkylimidazolium.

15 Claims, No Drawings

METHOD FOR PRODUCING ADAMANTANE

BACKGROUND OF THE INVENTION

1. Field of the Invention

This invention relates to a method for producing adamantane, more particularly to a method for producing adamantane in an acidic chloroaluminate ionic liquid.

2. Description of the Related Art

Adamantane (tricyclo[3,3,1,1$^{3,7}$]decane) is a colorless, non-toxic, crystalline compound. With a formula $C_{10}H_{16}$, it is a cycloalkane, and is also the simplest diamondoid. The chemical and physical properties thereof are as follows: melting point of 268° C., density of 1.07 g/cm$^3$, good heat stability, hydrophobicity (due to high symmetry of molecules), ease of sublimation, and good lubricity.

Since hydrogen atoms in adamantane are easily substituted, $S_N1$ nucleophilic substitution reaction and $S_E2$ electrophilic substitution reaction usually occur in adamantane. In particular conditions, adamantane can be converted into various derivatives through skeleton rearrangement, oxidation, or alkylation reaction such that adamantane and derivatives thereof have great potential usage in medicine, textile industry, catalyst, surfactant, photo-sensing material, etc. However, high manufacturing costs make the development of adamantane limited.

In general, conventional methods for producing adamantane include ring-closing method, aluminum(III) trichloride method, zeolite catalyzing method, and superacid method. However, the conventional methods have disadvantages. For example, the ring-closing method has disadvantages of complicated procedure, many undesired side reactions, necessity for protecting functional groups of reactants, long operation time, and low productivity.

Aluminum(III) trichloride method, zeolite catalyzing method, and superacid method all involve isomerization of tetrahydro dicyclopentadiene (THDCPD) into adamantane. In these methods, many side products are also produced along with adamantane such that selectivity for adamantane becomes relatively low.

Moreover, in the aluminum(III) trichloride method, a large amount of tar is produced so that productivity of adamantane is considerably decreased and the procedure for purifying adamantane becomes complicated. Moreover, recycling of $AlCl_3$ is difficult. In addition, before discharging $AlCl_3$, an alkaline solution is used to degrade the same so that a lot of waste is produced, thereby resulting in environmental problems. Although solid acids (e.g., $H_2SO_4$-treated $Al_2O_3$, $Al_2O_3$—$SiO_2$) are proposed to replace $AlCl_3$ for eliminating the environmental problems, they are not popularly employed because of low activity and short lifetime.

In addition, superacid catalysts are proposed for the isomerization reaction. For example, $B(OSO_2CF_3)_3$—$HSO_3CF_3$ is used to catalyze the isomerization reaction at 100° C. Although productivity of adamantane can be up to 47~65%, high corrosion of the superacid catalyst to the apparatus and immature technology for handling the superacid catalyst make the method unsuitable for industrial use.

Recently, a new kind of solvent, i.e., ionic solvent, has been proposed. The ionic solvents have many advantages. For example, they have no measurable vapor pressure, and hence can emit no volatile organic compounds so that operation thereof is much safer. Moreover, since the ionic solvents are usually not miscible with the reactants and products, recycling thereof and purification of the products become easier. In addition, the pH value thereof can be adjusted by modifying the proportion of components thereof. Specifically, the pH value of the ionic solvent depends on the components and the proportions of the components, in which acidity is determined by anions of the ionic solvent. For example, in the chloroaluminate(III) ionic solvent (composed of $AlCl_3$ and a quaternary ammonium halide/quaternary phosphonium halide), if the molar fraction of $AlCl_3$ is 0.5, $AlCl_4^-$ (having low acceptance of electron pairs) becomes dominant so that the chloroaluminate(III) ionic solvent serves as a weak Lewis acid. If the molar fraction of $AlCl_3$ is greater than 0.5, $Al_2Cl_7^-$ and $Al_3Cl_{10}^-$ are dominant so that the chloroaluminate(III) ionic solvent serves as a powerful Lewis acid.

In view of the aforesaid advantages, researches have focused on use of the ionic solvent in manufacturing adamantane. For example, in *Petrochemical Technology*, 31, vol. 5, 345-348 (2002), a method for producing adamantane in an ionic liquid is proposed, which includes transforming dicyclopentadiene (DCPD) into endo-tetrahydro dicyclopentadiene (endo-THDCPD) in an ionic liquid of 1-n-butyl-3-methylimidazolium chloride-$BF_4$ ([BMIM]Cl—[$BF_4$]) at 90~150° C. and 1.0~1.5 MPa, and isomerizing endo-THDCPD into exo-THDCPD and adamantane in an ionic liquid of 1-n-butyl-3-methylimidazolium chloride-$AlCl_3$ ([BMIM]Cl—[$AlCl_3$]) in the presence of hydrogen (4 MPa).

SUMMARY OF THE INVENTION

The object of the present invention is to provide a method for producing adamantane that can provide higher productivity for adamantane.

According to this invention, a method for producing adamantane includes isomerizing exo-tetrahydrodicyclopentadiene into adamantane in an acidic chloroaluminate ionic liquid composed of aluminum(III) trichloride and a quaternary ammonium halide.

DETAILED DESCRIPTION OF THE PREFERRED EMBODIMENTS

The preferred embodiment of a method for producing adamantane according to the present invention includes isomerizing exo-tetrahydrodicyclopentadiene (exo-THDCPD) into adamantane in an acidic chloroaluminate ionic liquid composed of aluminum(III) trichloride and a quaternary ammonium halide having a quaternary ammonium cation selected from a group consisting of tetraalkylammonium, dialkylpyridinium, and trialkylimidazolium. The alkyl group in tetraalkylammonium, dialkylpyridinium, and trialkylimidazolium is $C_nH_{2n+1}$, where n is a number between 0 and 18. The quaternary ammonium halide further has a halide ion selected from a group consisting of fluoride ion, chloride ion, bromide ion and iodide ion.

Preferably, the quaternary ammonium halide is pyridine hydrochloride.

The molar fraction of aluminum(III) trichloride in the acidic chloroaluminate ionic liquid ranges from 0.5 to 0.9, preferably, 0.55 to 0.85, and more preferably, 0.6 to 0.75.

Preferably, the reaction temperature ranges from 40 to 90° C., and more preferably, from 50 to 70° C., to avoid occurrence of undesired reactions which result in reduction of productivity and selectivity for adamantane.

The molar ratio of tetrahydrodicyclopentadiene to the quaternary ammonium halide/quaternary phosphonium halide ranges from 100 to 0.1, preferably, from 10 to 0.5, and more preferably, is 1.28.

The method of this invention is preferably conducted under an inert atmosphere. The gas in the inert atmosphere is inactive to the acidic chloroaluminate ionic liquid, reactants, and products. Preferably, the gas is nitrogen, helium, neon, and argon, and more preferably, is nitrogen. It should be noted that moisture is to be avoided in the reaction environment, and should be removed before performing the method.

Moreover, the isomerization reaction is preferably conducted at about 1 atm.

It should be noted that it is difficult to separate adamantane from the acidic chloroaluminate ionic liquid when adamantane is dispersed therein. To simplify the procedure, adamantane produced by the method of this invention is preferably dissolved in a solvent immediately after being produced. Therefore, a solvent used to dissolve adamantane is preferably included in the method of this invention. Since the reactant, exo-THDCPD, is in the form of a liquid and adamantane can be dissolved therein, the solvent can be dispensed with when an excess amount of exo-THDCPD is employed. On the other hand, when the solvent is employed in the method of this invention, the amounts of the solvent and exo-THDCPD can be adjusted based on reaction conditions as long as adamantane thus obtained can be dissolved.

Besides exo-THDCPD, endo-THDCPD in the form of solid can be used in this invention. If solid endo-THDCPD is used, a solvent for dissolving endo-THDCPD and adamantane is required in the method. Specifically, when endo-THDCPD is used as a starting material, endo-THDCPD should be dissolved in a solvent for conducting the reaction of transforming endo-THDCPD into exo-THDCPD and then into adamantane. The solvent used to dissolve endo-THDCPD and adamantane is not miscible with the acidic ionic liquid. Examples of the solvent include n-alkane, iso-alkane, neo-alkane, cycloalkane, and a hydrocarbon containing halogens. Preferably, the solvent is cyclohexane or n-heptane. Moreover, the concentration of endo-THDCPD ranges from 10 wt % to the saturated concentration, and more preferably, is 50 wt %. In addition, in order to completely dissolve adamantane thus produced in the solvent, rather than dispersing adamantane in the acidic chloroaluminate ionic liquid, the amount of adamantane thus produced should be controlled.

Regarding the reaction time, since the isomerization reaction starts immediately after THDCPD contacts the ionic liquid having a sufficient acidity, reaction time is not a controlling factor in the productivity of adamantane.

EXAMPLES

Preparation of Exo-THDCPD 0.5 part of the above acidic chloroaluminate ionic liquid was placed in a 70° C. oil-bath, and a mixture containing 16 g endo-THDCPD and cyclohexane at a weight ratio of 1:1 was added in the acidic ionic liquid, followed by undergoing an isomerization reaction at 400 rpm for one hour so as to form exo-THDCPD. The productivity is 96.7%. Alternatively, exo-THDCPD can be obtained from a commercially available product.

Preparation of Adamantane

Example 1

0.091 mole (10.58 g) PHC and 0.17 mole (22.675 g) $AlCl_3$ were mixed at 50° C. so as to form one part of the acidic ionic liquid, in which the molar fraction of $AlCl_3$ was 0.65. 0.1176 mole (16 g) exo-THDCPD was added into one part of the acidic ionic liquid (the molar ratio of exo-THDCPD to PHC is 1.28), followed by undergoing an isomerization reaction under conditions of 70° C., 1 atm, dried nitrogen atmosphere, and 400 rpm for an hour so as to form a liquid product which is immiscible with and is disposed above the acidic ionic liquid. The liquid product was taken out for analysis using gas chromomatography (HP6890, available from HP company, USA; column is a wall coated open tubular and non-polarity fused silica column available from Chrompack Company, CP-Sil 5CB) for calculating conversion rate and selectivity. The operating conditions of the analysis were as follows: injection volume was 0.2 μl; the temperature was kept at 50° C. during first 10 mins. Then, the temperature was increased at a rate of 8° C./min to 280° C., and was subsequently kept at 280° C. for 15 mins. The detector used was flame ionization detector (FID), and the detecting temperature was 250° C.

The operations of the following Examples 2 to 32 were similar to that of Example 1 except for the temperature, isomerization time, or preparation of the acidic ionic liquid (i.e., species of the reactants or molar fraction of $AlCl_3$)

Example 2

Isomerization time was 4 hours.

Example 3

Isomerization time was 6 hours.

Example 4

Isomerization time was 24 hours.

Example 5

Isomerization temperature was 60° C.

Example 6

Isomerization temperature was 60° C., and isomerization time was 4 hours.

Example 7

Isomerization temperature was 60° C., and isomerization time was 6 hours.

Example 8

Isomerization temperature was 60° C., and isomerization time was 24 hours.

Example 9

Isomerization temperature was 50° C., and isomerization time was 1 hour.

Example 10

Isomerization temperature was 50° C., and isomerization time was 4 hours.

Example 11

Isomerization temperature was 50° C., and isomerization time was 6 hours.

Example 12

Isomerization temperature was 50° C., and isomerization time was 24 hours.

Example 13

The molar fraction of $AlCl_3$ in the ionic liquid was 0.6. The "one part" of ionic liquid was obtained by mixing 0.091 mole (i.e., 10.58 g) PHC with 0.137 mole $AlCl_3$ (i.e., 18.322 g)).

Example 14

The molar fraction of $AlCl_3$ in the ionic liquid was 0.6. Isomerization time was 4 hours.

Example 15

The molar fraction of $AlCl_3$ in the ionic liquid was 0.6. Isomerization time was 6 hours.

Example 16

The molar fraction of $AlCl_3$ in the ionic liquid was 0.6. Isomerization time was 24 hours.

Example 17

The molar fraction of $AlCl_3$ in the ionic liquid was 0.75. The "one part" of the ionic liquid was obtained by mixing 0.091 mole (i.e., 10.58 g) PHC with 0.275 mole $AlCl_3$ (i.e., 36.64 g)).

Example 18

The molar fraction of $AlCl_3$ in the ionic liquid was 0.75. Isomerization time was 4 hours.

Example 19

The molar fraction of $AlCl_3$ in the ionic liquid was 0.75. Isomerization time was 6 hours.

Example 20

The molar fraction of $AlCl_3$ in the ionic liquid was 0.75. Isomerization time was 24 hours.

Example 21

TEAC was used to replace PHC.

Example 22

TEAC was used to replace PHC. Isomerization time was 4 hours.

Example 23

TEAC was used to replace PHC. Isomerization time was 6 hours.

Example 24

TEAC was used to replace PHC. Isomerization time was 24 hours.

Example 25

PHB (14.658 g) was used to replace PHC.

Example 26

PHB (14.658 g) was used to replace PHC. Isomerization time was 4 hours.

Example 27

PHB (14.658 g) was used to replace PHC. Isomerization time was 6 hours.

Example 28

PHB (14.658 g) was used to replace PHC. Isomerization time was 24 hours.

Comparative Example 1

BMIC (16 g) was used to replace PHC.

Comparative Example 2

BMIC (16 g) was used to replace PHC. Isomerization time was 4 hours.

Comparative Example 3

BMIC (16 g) was used to replace PHC. Isomerization time was 6 hours.

Comparative Example 4

BMIC (16 g) was used to replace PHC. Isomerization time was 24 hours.

Table 1 lists the conditions of Examples 1 to 28 and Comparative examples 1 to 4, the conversion rate of exo-THD-CPD, selectivity for THDCPD and adamantane, and productivity for adamantane.

As shown in Table 1, comparing Examples 1 to 4 and 21 to 28 with comparative examples 1 to 4, Examples 1 to 4 and 21 to 28 which use PHC, TEAC, and PHB as the halide component, respectively, exhibit higher productivity for adamantane than comparative examples 1 to 4 which use BMIC as the halide component. Examples 1 to 4 which use PHC as the halide component provide the most preferable productivity for adamantane.

Productivity for adamantane also increases with an increase in reaction temperature (see Examples 1 to 12) and an increase in molar fraction of $AlCl_3$ (comparing Examples 1 to 4, 13 to 16, and 17 to 20).

Moreover, selectivity for adamantane in most of the examples is greater than 70%, and achieves a stable level after about 4 hours. In addition, conversion rate and productivity increase with an increase in the reaction time.

TABLE 1

| Exp. | Reactant | Temp. (°C.) | Time (hr) | halide | Molar fraction of AlCl$_3$ | Conversion of the reactant Endo-THDCPD | Conversion of the reactant Exo-THDCPD | Selectivity Exo-THDCPD | Selectivity Adamantane | Productivity of adamantane |
|---|---|---|---|---|---|---|---|---|---|---|
| 1 | Exo- | 70 | 1 | PHC | 0.65 | — | 14.0 | — | 78.4 | 10.96 |
| 2 | THDCPD |  | 4 |  |  |  | 24.7 |  | 76.5 | 18.90 |
| 3 |  |  | 6 |  |  |  | 27.5 |  | 76.3 | 20.98 |
| 4 |  |  | 24 |  |  |  | 37.8 |  | 77.2 | 29.18 |
| 5 | Exo- | 60 | 1 | PHC | 0.65 | — | 6.8 | — | 100 | 6.8 |
| 6 | THDCPD |  | 4 |  |  |  | 15.7 |  | 77.7 | 12.20 |
| 7 |  |  | 6 |  |  |  | 18.1 |  | 77.0 | 13.94 |
| 8 |  |  | 24 |  |  |  | 27.7 |  | 76.9 | 21.30 |
| 9 | Exo- | 50 | 1 | PHC | 0.65 | — | 1.6 | — | 100 | 1.6 |
| 10 | THDCPD |  | 4 |  |  |  | 9.6 |  | 78.7 | 7.56 |
| 11 |  |  | 6 |  |  |  | 12.0 |  | 78.2 | 9.38 |
| 12 |  |  | 24 |  |  |  | 20.5 |  | 77.2 | 15.82 |
| 13 | Exo- | 70 | 1 | PHC | 0.6 | — | 2.2 | — | 82.2 | 1.81 |
| 14 | THDCPD |  | 4 |  |  |  | 13.8 |  | 67.4 | 9.30 |
| 15 |  |  | 6 |  |  |  | 16.0 |  | 62.1 | 9.94 |
| 16 |  |  | 24 |  |  |  | 21.4 |  | 61.2 | 13.10 |
| 17 | Exo- | 70 | 1 | PHC | 0.75 | — | 37.9 | — | 78.7 | 29.83 |
| 18 | THDCPD |  | 4 |  |  |  | 40.1 |  | 76.5 | 30.68 |
| 19 |  |  | 6 |  |  |  | 40.1 |  | 75.5 | 30.28 |
| 20 |  |  | 24 |  |  |  | 40.5 |  | 55.7 | 22.56 |
| 21 | Exo- | 70 | 1 | TEAC | 0.65 | — | 10.0 | — | 74.1 | 7.41 |
| 22 | THDCPD |  | 4 |  |  |  | 13.5 |  | 73.5 | 9.92 |
| 23 |  |  | 6 |  |  |  | 14.5 |  | 73.4 | 10.64 |
| 24 |  |  | 24 |  |  |  | 16.1 |  | 72.9 | 11.74 |
| 25 | Exo- | 70 | 1 | PHB | 0.65 | — | 14.4 | — | 77.4 | 11.15 |
| 26 | THDCPD |  | 4 |  |  |  | 20.8 |  | 76.1 | 15.83 |
| 27 |  |  | 6 |  |  |  | 21.2 |  | 76.1 | 16.13 |
| 28 |  |  | 24 |  |  |  | 22.4 |  | 76.1 | 17.05 |
| Comparative Examples | | | | | | | | | | |
| 1 | Exo- | 70 | 1 | BMIC | 0.65 | — | 2.4 | — | 100 | 2.4 |
| 2 | THDCPD |  | 4 |  |  |  | 8.0 |  | 67.3 | 5.38 |
| 3 |  |  | 6 |  |  |  | 9.1 |  | 70.6 | 6.42 |
| 4 |  |  | 24 |  |  |  | 12.5 |  | 70.3 | 8.79 |

In sum, the method of this invention obtains superior productivity and selectivity for adamantane using PHC, TEAC, or PHB as the halide component in the acidic ionic liquid. In addition, under optimum reaction conditions, i.e., temperature, molar fraction of AlCl$_3$, etc., productivity of adamantane can be further enhanced.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

What is claimed is:

1. A method for producing adamantane comprising:
isomerizing exo-tetrahydrodicyclopentadiene into adamantane in an acidic chloroaluminate ionic liquid composed of aluminum(III) trichloride and a quaternary ammonium halide.

2. The method according to claim 1, wherein said quaternary ammonium halide has a quaternary ammonium cation selected from a group consisting of tetraalkylammonium, dialkylpyridinium, and trialkylimidazolium.

3. The method according to claim 2, wherein the alkyl group in tetraalkylammonium, dialkylpyridinium, and trialkylimidazolium is $C_nH_{2n+1}$; and wherein said n is a number between 0 and 18.

4. The method according to claim 2, wherein said quaternary ammonium halide further has a halide ion selected from a group consisting of fluoride ion, chloride ion, bromide ion and iodide ion.

5. The method of claim 1, wherein the molar fraction of aluminum (III) trichloride in the acidic chloroaluminate ionic liquid ranges from 0.5 to 0.9.

6. The method of claim 5, wherein the molar fraction of aluminum(III) trichloride in the acidic chloroaluminate ionic liquid ranges from 0.6 to 0.75.

7. The method of claim 1, wherein the reaction is conducted at a reaction temperature ranging from 25 to 150° C.

8. The method of claim 7, wherein the reaction temperature ranges from 40 to 90° C.

9. The method of claim 8, wherein the reaction temperature ranges from 50 to 70° C.

10. The method of claim 1, wherein the molar ratio of exo-tetrahydrodicyclopentadiene to the quaternary ammonium halide ranging from 100 to 0.1.

11. The method of claim 10, wherein the molar ratio of exo-tetrahydrodicyclopentadiene to the quaternary ammonium halide ranges from 10 to 0.5.

12. The method of claim 11, wherein the molar ratio of exo-tetrahydrodicyclopentadiene to the quaternary ammonium halide is 1.28.

13. The method of claim 1, wherein the reaction is conducted under an inert atmosphere.

14. The method of claim 13, wherein the isomerization is conducted under a nitrogen atmosphere.

15. The method of claim 1, wherein the isomerization reaction is conducted at 1 atm.

* * * * *